(12) United States Patent
Beltrame et al.

(10) Patent No.: US 10,233,141 B2
(45) Date of Patent: Mar. 19, 2019

(54) PROCESS FOR THE PREPARATION OF FATTY ACID ALKYL ESTERS

(71) Applicant: Southern Biofuel Technology Pty Ltd, Melbourne (AU)

(72) Inventors: Reno Emilio Beltrame, Melbourne (AU); Patrick Perlmutter, Melbourne (AU); Ketav Kulkarni, Melbourne (AU)

(73) Assignee: SOUTHERN BIOFUEL TECHNOLOGY PTY LTD, Geelong West, Melbourne (AU)

( * ) Notice: Subject to any disclaimer, the term of this patent is extended or adjusted under 35 U.S.C. 154(b) by 0 days.

(21) Appl. No.: 15/317,232

(22) PCT Filed: Jun. 12, 2015

(86) PCT No.: PCT/AU2015/050324
§ 371 (c)(1),
(2) Date: Dec. 8, 2016

(87) PCT Pub. No.: WO2015/188233
PCT Pub. Date: Dec. 17, 2015

(65) Prior Publication Data
US 2017/0113996 A1    Apr. 27, 2017

(30) Foreign Application Priority Data

Jun. 13, 2014 (AU) ................. 2014902260

(51) Int. Cl.
| | | |
|---|---|---|
| *C07C 67/08* | (2006.01) | |
| *C07C 67/02* | (2006.01) | |
| *C11C 3/10* | (2006.01) | |
| *C07C 67/03* | (2006.01) | |
| *C10L 1/02* | (2006.01) | |
| *C11B 3/04* | (2006.01) | |
| *C11B 3/08* | (2006.01) | |
| *C11C 3/00* | (2006.01) | |
| *C07C 69/003* | (2006.01) | |
| *C11B 3/00* | (2006.01) | |

(52) U.S. Cl.
CPC .............. *C07C 67/08* (2013.01); *C07C 67/02* (2013.01); *C07C 67/03* (2013.01); *C07C 69/003* (2013.01); *C10L 1/026* (2013.01); *C11B 3/00* (2013.01); *C11B 3/04* (2013.01); *C11B 3/08* (2013.01); *C11C 3/003* (2013.01); *C11C 3/10* (2013.01); *C10L 2200/0476* (2013.01); *Y02E 50/13* (2013.01)

(58) Field of Classification Search
CPC ......... C07C 67/03; C07C 67/08; C07C 67/10; C07C 69/52; C07C 67/02; C07C 69/003; C11C 3/00; C11C 3/003; C11B 3/00; C11B 3/04
See application file for complete search history.

(56) References Cited

U.S. PATENT DOCUMENTS

| | | | | |
|---|---|---|---|---|
| 2,467,095 A | * | 4/1949 | Noffsinger | C07C 67/00 560/1 |
| 3,128,294 A | * | 4/1964 | Stirton | C07C 309/17 510/359 |
| 3,172,905 A | * | 3/1965 | Eckert | B01J 31/0225 502/168 |
| 8,440,847 B2 | * | 5/2013 | Nang | C10L 1/026 554/167 |
| 2009/0235574 A1 | * | 9/2009 | Earle | B01J 31/0279 44/308 |

FOREIGN PATENT DOCUMENTS

| | | | | |
|---|---|---|---|---|
| CN | 101343245 | * | 1/2009 | ........... C07C 303/32 |

OTHER PUBLICATIONS

Hayyan, A. et al., Ethane sulfonic acid-based esterification of industrial acidic crude palm oil for biodiesel production, 2011, Bioresource Technology, vol. 102, pp. 9564-9570 (Year: 2011).*
CN1010343245, Yun Fang et al., Mehtod for preparing fatty acid methyl ester sulphonic salt with low-disodium salt content by using earlier sulfonation and later esterificationtechnique, 2009, English translation 5 pages (Year: 2009).*

* cited by examiner

*Primary Examiner* — Yate' K Cutliff
(74) *Attorney, Agent, or Firm* — K&L Gates LLP

(57) ABSTRACT

The present invention broadly relates to a process for preparing fatty acid alkyl esters from fat-containing feedstocks using sulfonated fatty acid catalysts.

27 Claims, No Drawings

PROCESS FOR THE PREPARATION OF FATTY ACID ALKYL ESTERS

FIELD OF THE INVENTION

The present invention broadly relates to a process for preparing fatty acid alkyl esters from fat-containing feedstocks.

BACKGROUND OF THE INVENTION

Fatty acid alkyl esters find use in a number of industries, for example mining (as collectors), agriculture (as adjuvants) and energy (biodiesel). Fatty acid alkyl esters are typically prepared from feedstocks including vegetable oil, animal fat and used cooking oil by converting the constituent fatty acid triglycerides and any free fatty acids. Typically, the esters are short-chain esters such as methyl esters.

Conventional processes for producing fatty acid alkyl esters from triglyceride-based oils typically involve, in a first step, heating the oils at about 60-65° C. in the presence of sulfuric acid and a large excess of methanol in order to convert free fatty acids into methyl esters. A key requirement for this step is that the amount of water present is no more than 1%. Under these conditions minimal transesterification occurs. In a second step, transesterification of triglycerides into the corresponding methyl esters employing sodium methoxide in methanol is performed. The second step is usually repeated in order to maximise conversion and yield.

The present inventors have surprisingly discovered that fat-containing feedstocks having a broad range of free fatty acid contents can be efficiently esterified and transesterified under aqueous conditions by use of selected sulfonated fatty acid derivatives as catalysts.

SUMMARY OF THE INVENTION

In a first aspect the present invention provides a process for preparing fatty acid alkyl esters comprising:
 i) forming a mixture comprising a fat-containing feedstock, an alcohol and a sulfonated fatty acid derivative of the formula (I), or a salt thereof:

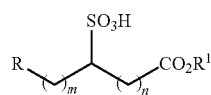
(I)

wherein:
n is an integer between 0 and 7,
m is an integer between 0 and 17,
R is hydrogen or methyl,
$R^1$ is hydrogen or $C_1$-$C_6$ alkyl,
 ii) allowing the mixture in step i) to react so as to produce a mixture comprising fatty acid alkyl esters;
 iii) isolating the fatty acid alkyl esters obtained in step ii).

The fat-containing feedstock may comprise at least 20%, at least 30%, at least 40%, at least 50%, at least 60%, at least 70%, at least 80%, at least 90%, or at least 95%, by weight of free fatty acids.

The fat-containing feedstock may be a triglyceride-containing feedstock, for example a triglyceride-containing oil.

The alcohol may be present in the mixture in an amount between about 10% and about 60%, or in an amount between about 15% and about 60%, or in an amount between about 15% and about 40%, or in an amount between about 15% and about 30%, by weight.

The sulfonated fatty acid derivative may be present in the mixture in an amount between about 0.05% and about 5%, or in an amount between about 0.5% and about 2.5%, or in an amount between about 0.1% and about 5%, or in an amount between about 0.1% and 2%, by weight.

The mixture in step i) may further comprise an acid. The acid may be present in the mixture in an amount between about 0.5% and about 5%, or in an amount between about 0.5% and about 3%, or in an amount between about 0.5% and about 2.5%, or in an amount between about 1% and about 2%, by weight.

The mixture in step i) may further comprise water. Water may be present in an amount of up to about 10%, or in an amount of up to about 5%, or in an amount of up to about 2%, or in an amount of up to about 1%, by weight. In some embodiments water may be present in an amount between about 0.5% and about 5%, or in an amount between about 1% and about 5%, or in an amount between about 1% and about 2%, by weight.

The fatty acid alkyl esters may be $C_1$-$C_{12}$ alkyl esters or mixtures thereof. In some embodiments the fatty acid alkyl esters are $C_1$-$C_6$ alkyl esters, or mixtures thereof. In one embodiment the fatty acid alkyl esters are methyl esters.

The alcohol may be a $C_1$-$C_{12}$ alcohol, or a mixture thereof. In some embodiments the alcohol is a $C_1$-$C_6$ alcohol, or a mixture thereof. In one embodiment the alcohol is methanol.

The acid may be a strong acid, for example, sulfuric acid.

Step ii) may comprise heating the mixture.

Typically, the process is performed at atmospheric pressure.

In the sulfonated fatty acid derivative of the formula (I) or salt thereof, m may be an integer between 6 and 17, or an integer between 8 and 17, or an integer between 10 and 17 or an integer between 11 and 15.

In the sulfonated fatty acid derivative of the formula (I) or salt thereof, n may be an integer between 0 and 6, 0 and 4, or 0 and 3. In one embodiment n is 0, 1 or 2. In another embodiment n is 0 or 1.

In the sulfonated fatty acid derivative of the formula (I) or salt thereof, $R^1$ may be $C_1$-$C_6$ alkyl. In one embodiment $R^1$ is methyl.

In the sulfonated fatty acid derivative of the formula (I) or salt thereof, R may be methyl.

In some embodiments m is an integer between 8 and 17, n is 0, 1 or 2 and R and $R^1$ are methyl.

In other embodiments m is an integer between 8 and 15, n is 0 and R and $R^1$ are methyl.

In other embodiments m is an integer between 11 and 15, n is 0 and R and $R^1$ are methyl.

The mixture in step i) may comprise a plurality of sulfonated fatty acid derivatives of the formula (I). In one embodiment the mixture comprises a plurality of $C_{14}$-$C_{18}$ α-sulfonated fatty acid methyl esters.

In still a further embodiment the sulfonated fatty acid derivative is $C_{16}$-$C_{18}$alkyl $CH(SO_3H)COOCH_3$ or a salt thereof, for example α-MES.

The process may further comprise pre-treatment of the fat-containing feedstock used in step i), for example the fat-containing feedstock may be bleached and/or degummed prior to use in step i).

In some embodiments the process further comprises:
 iv) forming a mixture comprising the fatty acid alkyl esters obtained following step iii), unreacted triglycerides or unreacted free fatty acids, an alcohol and a sulfonated fatty acid derivative of the formula (I) as defined above;

v) allowing the mixture in step iv) to react such that at least some of the triglycerides or at least some of the free fatty acids are converted into fatty acid alkyl esters;

vi) isolating the fatty acid alkyl esters from the mixture following step v).

In these embodiments the alcohol may be an anhydrous alcohol and the mixture in step iv) may further comprise an acid. Step v) may comprise heating the mixture.

In some embodiments the process further comprises:

vii) treating the fatty acid alkyl esters obtained following step iii) or step vi) with a base so as to neutralise residual acid.

In some embodiments, the process further comprises:

viii) base-catalysed transesterification following steps iii), vi) or vii) so as to convert at least some unreacted triglycerides present with the fatty acid alkyl esters into fatty acid alkyl esters.

ix) isolating the fatty acid alkyl esters following step viii).

The fatty acid alkyl esters obtained following steps iii), vi) or ix) may be suitable for use as biodiesel with, or without further purification.

The process may further comprise distilling the fatty acid alkyl esters obtained following steps iii), vi) or ix).

In some embodiments fatty acid alkyl esters isolated in one or more of steps iii), vi) or ix) may not be subjected to further purification.

In a second aspect the present invention provides fatty acid alkyl esters whenever prepared by the process of the first aspect.

In a third aspect the present invention provides use of fatty acid alkyl esters of the second aspect as biodiesel.

DEFINITIONS

The following are some definitions that may be helpful in understanding the description of the present invention. These are intended as general definitions and should in no way limit the scope of the present invention to those terms alone, but are put forth for a better understanding of the following description.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps. Thus, in the context of this specification, the term "comprising" means "including principally, but not necessarily solely".

In the context of this specification the term "about" is understood to refer to a range of numbers that a person of skill in the art would consider equivalent to the recited value in the context of achieving the same function or result.

In the context of this specification the terms "a" and "an" are used herein to refer to one or to more than one (i.e at least one) of the grammatical object of the article. By way of example, "an element" means one element or more than one element.

In the context of this specification the term "consisting essentially of" is intended to exclude a step or steps that would materially affect the process or product of the process to which it refers.

In the context of this specification the terms "$C_1$-$C_{12}$ alcohol" and "$C_1$-$C_6$ alcohol" are taken to mean straight chain or branched chain monovalent saturated hydrocarbon groups having between 1 and 12 or 1 and 6 carbon atoms and a single hydroxy group. Examples of $C_1$-$C_{12}$ alcohols include, but are not limited to, methanol, ethanol, 1-propanol, 2-propanol, isopropanol, 1-butanol, 2-butanol, isobutanol, tert-butanol, isopentanol, 1-pentanol, 2-pentanol, 2-methyl-1-pentanol, 4-methyl-1-pentanol, 3-methyl-2-pentanol, 1-hexanol, 2-hexanol, 3-hexanol, 1-heptanol, 3,4-dimethyl-1-heptanol, 2-octanol, 1-decanol, 3-dodecanol and the like.

In the context of this specification, the terms "$C_1$-$C_{12}$ alkyl" and "$C_1$-$C_6$ alkyl" are taken to mean straight chain or branched chain monovalent saturated hydrocarbon groups having between 1 and 12 or 1 and 6 carbon atoms. Examples of $C_1$-$C_{12}$ alkyl groups include, but are not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, dodecyl and the like.

DETAILED DESCRIPTION OF THE INVENTION

In one aspect the present invention provides a process for preparing fatty acid alkyl esters comprising or consisting essentially of:

i) forming a mixture comprising a fat-containing feedstock, an alcohol and a sulfonated fatty acid derivative of the formula (I), or a salt thereof:

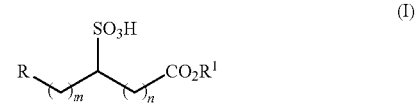

(I)

wherein:

n is an integer between 0 and 7, m is an integer between 0 and 17,

R is hydrogen or methyl, $R^1$ is hydrogen or $C_1$-$C_6$ alkyl, ii) allowing the mixture in step i) to react so as to produce a mixture comprising fatty acid alkyl esters;

iii) isolating the fatty acid alkyl esters obtained in step ii).

The present invention is predicated on the surprising finding by the inventors that fat-containing feedstocks having a broad range of free fatty acid content can be efficiently esterified and transesterified under aqueous conditions by use of selected sulfonated fatty acid derivatives as catalysts. With some feedstocks it is possible to achieve at least 90% conversion in a single reaction step. Current processes used for preparing fatty acid alkyl esters at atmospheric pressure typically only tolerate free fatty acid levels of up to about 30% in the feedstock. Where the free fatty acid content rises above about 30% water generated from esterification retards the rate of further esterification. In addition, little if any transesterification occurs. Utilising the process of the present invention fatty acid alkyl esters having acceptable acid values and triglyceride levels can be obtained in less steps and in less time compared to when the catalyst is absent, and in some embodiments, in a single reaction step. Without wishing to be bound by theory the inventors postulate that the catalytic activity of the sulfonated fatty acid derivatives of formula (I) are not inhibited by the presence of water, meaning that the catalyst performs effectively in aqueous conditions. It was also surprisingly discovered that the presence of water is actually beneficial because it reduces colouration of the oil during the process. Because the catalyst is able to perform effectively in aqueous conditions the process of the present invention enables the use of a much wider range of fat-containing feedstocks for preparing fatty acid alkyl esters compared to prior art processes, including very low quality, cheap feedstocks containing high amounts of free fatty acids (for example palm sludge oil and grease trap waste).

Non-limiting examples of fat-containing feedstocks suitable for use in the present invention include palm oil sludge, vegetable oils (for example corn oil, peanut oil, soybean oil, cotton seed oil, rice bran oil, jatropha oil, sunflower oil, coconut oil, rapeseed oil, linseed oil, palm seed oil, canola oil and the like), animal fats (for example tallow and lard), waste cooking oil, grease trap waste, fish oil and microbial oil (for example yeast or algal oil). In some embodiments the fat-containing feedstock comprises at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or at least 99%, by weight of free fatty acids. In some embodiments the fat-containing feedstock is a triglyceride-containing feedstock, for example a triglyceride-containing oil. The triglyceride-containing feedstock may comprise free fatty acids in any of the amounts noted above.

In some embodiments, the fat-containing feedstock used in the process may be pretreated. Pre-treatment may be appropriate where the feedstock is contaminated with gums, odourous or intractable matter and/or where the feedstock is very dark in colour. Grease trap waste and palm oil sludge are examples of feedstocks that may require pre-treatment. In some embodiments pre-treatment involves bleaching and/or degumming. Degumming may be achieved by, for example, treating the feedstock with phosphoric acid and water. Bleaching may be carried out by, for example, treating the feedstock with chlorite. Those skilled in the art will be familiar with alternative methods for degumming and bleaching fat-containing feedstocks.

Fatty acid alkyl esters prepared in accordance with the process of the invention may be $C_1$-$C_{12}$ alkyl esters or mixtures thereof. In some embodiments the fatty acid alkyl esters are $C_1$-$C_6$ alkyl esters for example, methyl, ethyl, propyl, isopropyl, butyl, t-butyl etc. esters or mixtures thereof, such as for example fusel alcohol esters. Typically, fatty acid alkyl esters prepared in accordance with the process are methyl or ethyl esters.

The alcohol used in the process of the present invention is dependent on the type of fatty acid alkyl esters that are to be prepared. For example, if it is desired to prepare fatty acid methyl esters then the alcohol will be methanol. In some embodiments the alcohol is a $C_1$-$C_{12}$ alcohol or a mixture thereof. In other embodiments the alcohol is a $C_1$-$C_6$ alcohol, for example, methanol, ethanol, propanol, isopropanol, butanol, t-butanol, pentanol etc., or a mixture thereof, such as for example fusel alcohol. Typically, the alcohol is methanol or ethanol.

The process of the present invention does not require anhydrous conditions, and therefore permits the use of aqueous alcohols in step i), such as fusel alcohol or waste ethanol. Because aqueous alcohols are considerably cheaper than anhydrous alcohols the process of the present invention offers significant costs savings compared to known processes that require careful control over the amount of water present during esterification. The inventors have found that low-cost mixed aqueous alcohols such as fusel alcohol are suitable for use in the process. It has also been found that the alcohol can be recovered at the completion of the process and then re-used, in some instances without purification. Alternatively, the recovered alcohol can be distilled until it reaches a concentration of about 80% and then re-used in the process.

The alcohol may be present in the mixture in step i) in an amount between about 10% and about 60%, or in an amount between about 15% and about 60%, or in an amount between about 15% and about 40%, or in an amount between about 20% and about 40%, or in an amount between about 20% and about 30% by weight.

The weight ratio of fat-containing feedstock to alcohol may be in the range of about 2:1 to about 10:1, preferably about 5:1.

In other embodiments the process may be performed using anhydrous alcohols in step i), however as will be appreciated by those skilled in the art this will add considerably to the cost of performing the process thereby reducing its economic viability.

Where the mixture in step i) further comprises water, the water may be present in an amount of up to about 10%, or in an amount of up to about 8%, or in an amount of up to about 6%, or in an amount of up to about 5%, or in an amount of up to about 2%, or in an amount of up to about 1%, by weight. In some embodiments water is present in an amount between about 0.05% and about 10%, or in an amount between about 0.05% and about 5%, or in an amount between about 0.5% and about 3%, or in an amount between about 1% and about 6%, or in an amount between about 1% and about 5%, or in an amount between about 1% and about 3%, or in an amount between about 1% and about 2%, by weight.

In step i) water may be introduced into the mixture as part of an aqueous alcohol mixture and/or may be added to the mixture neat.

Where the mixture in step i) further comprises an acid, the acid may be present in the mixture in an amount between about 0.05% and about 5%, or in an amount between about 0.5% and about 5%, or in an amount between about 0.5% and about 3%, or in an amount between about 0.5% and about 2.5%, or in an amount between about 1% and about 2%, by weight. Persons skilled in the art will readily appreciate acids that are suitable for use in the process, for example hydroiodic acid, hydrochloric acid, hydrobromic acid, nitric acid, sulfuric acid, phosphoric acid and the like. Preferably the acid is a strong acid. In one embodiment the acid is sulfuric acid.

The sulfonated fatty acid derivative of the formula (I) has the following structure:

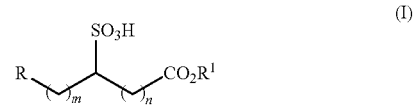

(I)

wherein n is an integer between 0 and 7, m is an integer between 0 and 17, R is hydrogen or methyl and $R^1$ is hydrogen or $C_1$-$C_6$ alkyl, or a salt thereof.

Exemplary salts of the sulfonated fatty acid derivatives include alkali metal salts (i.e lithium, potassium, sodium and caesium) and ammonium salts. Other suitable salts will be readily apparent to those skilled in the art. In one embodiment the sulfonated fatty acid derivatives are present in salt form, for example as sodium salts.

Sulfonated fatty acid derivatives of the formula (I) may be prepared by methods known to those skilled in the art, for example by a-sulfonation of the corresponding fatty acid derivatives. Sulfonated fatty acid derivatives of the formula (I) are also commercially available.

In some embodiments the catalyst is recovered when the process is completed.

The sulfonated fatty acid ester derivative of the formula (I) or salt thereof, may be present in the mixture in steps i) and iv) in an amount between about 0.05% and about 5%, or in an amount between about 0.2% and about 5%, or in an amount between about 0.5% and about 5%, or in an amount between about 0.5% and about 3%, or in an amount between about 0.5% and about 2%, by weight. In an alternative embodiment the sulfonated fatty acid ester derivative of the formula (I) or salt thereof may be present in the mixture in an amount up to about 5%, 4%, 3%, 2% or 1%, by weight.

Step ii) may comprise heating the mixture so as to increase the rate of reaction. In one embodiment the mixture is heated at the boiling point of the alcohol or mixture of alcohols. In other embodiments the mixture is heated at a temperature that is about 5 to 10° C. below the boiling point of the alcohol or mixture of alcohols. In further embodiments step ii) may comprise heating the mixture at a temperature between about 40 and 100° C., or at a temperature between about 50 and 90° C.

Step ii) may comprise heating the mixture for a period of time between about 1 hour and about 50 hours, or between about 1 hour and about 30 hours, or between about 5 hours and about 20 hours, or between about 4 hours and about 24 hours, or between about 4 hours and about 22 hours, or between about 4 hours and about 30 hours, or between about 1 hour and about 5 hours, or between about 1 hour and about 4 hours, or between about 1 hour and about 3 hours, or between about 1 hour and about 2 hours, or between about 12 hours and about 24 hours, or between about 12 hours and about 30 hours.

In some embodiments, where it is desired to obtain very high purity fatty acid alkyl esters and/or where the feedstock comprises very high amounts of free fatty acids (for example greater than about 80%), the fatty acid alkyl esters obtained in step iii) may be recycled through the process. Typically, this recycling serves to convert at least some of the unreacted triglycerides and/or at least some of the unreacted free fatty acids present with the fatty acid alkyl esters obtained following step iii), into fatty acid alkyl esters. Put another way, the recycling serves to enrich the purity of the fatty acid alkyl esters.

Accordingly, the process may further comprise:

iv) forming a mixture comprising the fatty acid alkyl esters obtained following step iii), unreacted triglycerides or unreacted free fatty acids, an alcohol and a sulfonated fatty acid derivative of the formula (I) as defined above;

v) allowing the mixture in step iv) to react such that at least some of the triglycerides or at least some of the free fatty acids are converted into fatty acid alkyl esters;

vi) isolating the fatty acid alkyl esters from the mixture following step v).

The mixture in step iv) may further comprise an acid as described above for step i). Step v) may comprise heating the mixture as described above for step ii). Typically, step v) is performed at atmospheric pressure. The amounts of sulfonated fatty acid derivative of the formula (I), acid and alcohol may be as defined above for step i). In one embodiment, the alcohol used in step iv) is anhydrous so as to optimise the conversion of triglycerides and/or free fatty acids to fatty acid alkyl esters. In some embodiments however, the mixture in step iv) may further comprise water as described above for step i).

In some embodiments the fatty acid alkyl esters obtained following steps iii) and vi) are treated with a base (such as for example methoxide) to neutralise residual acid. As well as removing residual acid, this step also reduces the water content of the fatty acid alkyl esters, which is advantageous where a base-catalysed transesterification step is to be performed.

In other embodiments, where it is desired to obtain very high purity fatty acid alkyl esters and/or where the feedstock comprises very high amounts of free fatty acids (for example greater than about 80%), the process further comprises:

viii) base-catalysed transesterification following steps iii), vi) or vii) so as to convert at least some unreacted triglycerides present with the fatty acid alkyl esters into fatty acid alkyl esters.

ix) isolating the fatty acid alkyl esters following step viii).

Step viii) may be performed by conventional methods known to those skilled in the art, for example treatment with an alcoholate anion in an alcohol solvent, for example sodium methoxide in methanol.

The process may comprise steps iv) to vi) where the feedstock comprises a significant amount of intractable foreign matter that must be removed. In such a case performance of steps i) to iii) produces a mixture that readily separates into a top phase, a small intermediate sludge phase and a bottom aqueous phase. The aqueous phase may be retained for subsequent re-use. The sludge phase containing the intractable foreign matter is disposed or used for composting. The desirable top phase can then be subjected to steps iv) to vi). The top phase comprising the esters can be used without further purification or washed with water. Alternatively, the top phase may be subjected to steps viii) and ix) using minimal amounts of alkaline catalyst and methanol to produce very high purity esters.

Isolation of the fatty acid alkyl esters (steps iii), vi) and ix)) may be performed by methods known to those skilled in the art. Typically, an oil layer comprising the fatty acid alkyl esters is separated from an aqueous layer after completion and washed with water. The oil may then be dried under vacuum so as to remove low molecular weight volatiles, such as alcohols, ethers, aldehydes and/or ketones.

The inventors have found that performance of steps i) to iii) utilising feedstocks with high free fatty acid content (for example about 50% to 70%) provides fatty acid alkyl esters at conversion rates above about 95%. Accordingly, steps iv) to ix) may only be required where the feedstock comprises very high amounts of free fatty acids (for example greater than 80%) and/or where the intended use requires very high purity fatty acid alkyl esters, such as for example in biodiesel applications. Typically, the Australian Biodiesel Standard requires an ester content of at least 96.5% (based on the EU Standard: prEN 14214).

Fatty acid alkyl esters isolated in steps iii) and/or vi) may have a purity of at least about 60%, or at least about 70%, or at least about 80%, or at least about 85%, or at least about 90%, or at least about 95%, or a purity in the range of about 80% and 85%, 85% and 90%, 90% and 99%, or 95% and 99%. Typically, the purity of the fatty acid alkyl esters obtained will be dependent on the quality of the fat-containing feedstock.

Fatty acid alkyl esters isolated in steps iii), step vi) or step ix) may have an acid value in the range of about 0.1 and 10 mg KOH/g, or in the range of about 0.1 and 5 mg KOH/g, or in the range of about 0.1 and 2 mg KOH/g of oil.

Fatty acid alkyl esters find use in, or are precursors to compounds used in, many industrial applications for example in graffiti removal products, as adjuvants for herbicides, as collectors in the mining industry and in biodiesel applications. Fatty acid alkyl ester compositions will require different levels of purity depending on their intended use. For example, strict limits are set on the amount of free fatty acids present in fatty acid alkyl ester compositions intended for use in biodiesel applications. In contrast, the presence of up to 20% of free fatty acids in fatty acid alkyl ester compositions intended for use as collectors is desirable. The process of the present invention is sufficiently flexible so as to allow efficient and cost effective preparation of fatty acid alkyl esters that are suitable for use across a range of different applications.

For example, the process may be used to prepare fatty acid alkyl esters suitable for use as collectors from grease trap waste by performing steps i), ii) and iii) (and optionally steps (iv), (v) and (vi)) using a cheap aqueous alcohol, such as fusel alcohol or waste ethanol. The extent of esterification and transesterification is such that no further purification of the fatty acid alkyl esters is required prior to use. If it is desired to provide higher purity fatty acid alkyl esters, steps i) to iii) can be followed by steps iv) to vi).

In another embodiment the process may be used to prepare fatty acid alkyl esters suitable for use as biodiesel from grease trap oil by performing steps i), ii) and iii) using aqueous methanol and distilling the resultant fatty acid alkyl esters obtained. The distilled esters may be used as biodiesel. Depending on the feedstock used, it is also possible to produce fatty acid alkyl esters that are suitable for use as biodiesel without any further purification by performing steps i), ii) and iii) only. Feedstocks of this type include high purity acid oils derived from purification of edible vegetable oils.

In an alternative embodiment, the process may be used to prepare fatty acid alkyl esters suitable for use as biodiesel from palm oil sludge by performing steps i) to iii), vii), viii) and ix). No further purification is required. In this embodiment, step viii) is preferably performed by base-catalysed transesterification using methoxide and methanol. Base-catalysed transesterification calls for the use of anhydrous alcohols. Because considerable transesterification occurs in step ii) of the process, the amount of anhydrous methanol required in order to convert any remaining triglycerides to fatty acid alkyl esters is much less than known processes, thereby further minimising costs associated with performing the process.

In still a further embodiment the process may be used to prepare fatty acid alkyl esters suitable for use as biodiesel from palm sludge oil utilising steps i) to ix).

EXAMPLES

The invention will now be described in more detail, by way of illustration only, with respect to the following examples. The examples are intended to serve to illustrate this invention and should not be construed as limiting the generality of the disclosure of the description throughout this specification.

In the following examples the catalyst used was a mixture of $C_{14}$-$C_{18}$ α-sulfonated fatty acid methyl esters.

Example 1

Preparation of Fatty Acid Methyl Esters from Grease Trap Oil having High Free Fatty Acid Content Utilising a Catalyst of Formula (I)

To a 1 litre three-necked round-bottom flask was added 500 grams of bleached and rinsed grease trap oil. The oil had a free fatty acid content of about 78% and an acid value of 156. 50.0 grams of 20% sulfuric acid in methanol, 93.3 grams of 91.1% methanol, 3.9 grams of water and 5.0 grams of catalyst were then added. The flask was equipped with a water-cooled condenser, thermometer, stoppered injection/sampling point and a magnetic stirrer. The mixture in the flask was heated to a temperature of 67° C. for a period of 2 hours. After this time period the acid value was 13.2 (after 1 hour the acid value was 27.7). Heating was ceased and the reaction was allowed to stand leading to phase separation. The upper layer comprising the esters was separated. To this upper layer was added 50.0 grams of 20% sulfuric acid in methanol, 43.0 grams of dry methanol and 5.0 grams of catalyst. The mixture in the flask was heated to a temperature of 71° C. for a period of 2 hours. Heating was ceased and the reaction was allowed to stand leading to phase separation. The upper layer comprising the esters was separated and washed with 25.0 grams of water. The recovered product is an almost clear liquid with an acid value of 3.4. Thin layer chromatography analysis of the product shows mostly esters (i.e. >90%) with very low triglycerides and low free fatty acids.

After completion of the first esterification (2 hours), a 10 g representative sample of the mixture was removed. The sample was kept in a stoppered tube at 50 to 60° C. in a water bath and shaken frequently over a period of 8 hours. It was then left to stand in the bath for about 16 hours, after which time two very distinct phases resulted. A sample of the clear and bright top phase had an acid value of 3.5. This demonstrates that a second esterification may be desirable in order to minimise costly reactor time. However performance of steps i) to iii) only, produce a very high conversion in a single reaction step.

Example 2

Preparation of Fatty Acid Methyl Esters from Grease Trap Oil having High Free Fatty Acid Content in the Absence of a Catalyst of Formula (I)

To a 1 litre three-necked round-bottom flask was added 500 grams of bleached and rinsed grease trap oil. The oil had a free fatty acid content of about 78% and an acid value of 156. 50.0 grams of 20% sulfuric acid in methanol, 93.3 grams of 91.1% methanol and 3.9 grams of water were then added. The flask was equipped with a water-cooled condenser, thermometer, stoppered injection/sampling point and a magnetic stirrer. The mixture in the flask was heated to a temperature of 67° C. for a period of 2 hours. After this time period the acid value was 40.7 (after 1 hour the acid value was 53.3). Heating was ceased and the reaction was allowed to stand leading to phase separation. The upper layer comprising the esters was separated. To this upper layer was added 53.7 grams of 20% sulfuric acid in methanol and 43.0 grams of dry methanol. The mixture in the flask was heated to a temperature of 71° C. for a period of 2 hours. After this time period the acid value was 24.0. Heating was ceased and the reaction was allowed to stand leading to phase separation. The upper layer comprising the esters was separated. To this upper layer was added 46.3 grams of 20% sulfuric acid in methanol and 52.0 grams of dry methanol. The mixture in the flask was heated to a temperature of 71° C. for a period of 8 hours. The upper layer comprising the esters was separated and washed with 25.0 grams of water. The recovered product is hazy and a very dark brown colour with an acid value of 4.0. Thin layer chromatography analysis of the product shows mostly esters (i.e. >90%) with some triglycerides and low free fatty acids.

It is apparent that when the catalyst is omitted an extra esterification step and a significantly longer reaction time is required in order to achieve a similar acid value to that obtained when using the catalyst. Importantly however, notwithstanding the extra step and longer reaction time the amount of triglyceride present in the product remains higher when the catalyst is omitted.

Example 3

Conventional Transesterification of the Product Obtained in Example 2

The product from Example 2 was subjected to a neutralisation step followed by a conventional transesterification as follows.

554 grams of the product from Example 2 was neutralised by stirring with 9.2 grams of 30% sodium methoxide for 30 minutes at 40° C. Stirring was ceased and the mixture was allowed to stand for about 60 minutes. The bottom layer was drained. The upper layering containing the esters had an acid value of 0.95. 50.0 grams of dry methanol and 10.0 grams of 30% sodium methoxide were added to the upper layer and the resulting mixture heated at 60° C. for 60 minutes. The product is separated and washed twice with 25.0 grams of water. The acid value was 0.55. Thin layer chromatography analysis of the product shows mostly esters with medium to low triglycerides and low free fatty acids. For use as biodiesel this product requires a further transesterification in order to reduce the triglyceride level.

Example 4

Conventional Transesterification of the Product Obtained in Example 1

The product from Example 1 was subjected to a neutralisation step followed by a conventional transesterification as follows.

564 grams of the product from Example 2 was neutralised by stirring with 8.0 grams of 30% sodium methoxide for 30 minutes at 40° C. Stirring was ceased and the mixture was allowed to stand for about 60 minutes. The bottom layer was drained. The upper layering containing the esters had an acid value of 0.5. 25.0 grams of dry methanol and 10.0 grams of 30% sodium methoxide were added to the upper layer and the resulting mixture heated at 60° C. for 60 minutes. The product was separated and washed twice with 25.0 grams of water. The acid value was 0.43. Thin layer chromatography analysis of the product shows mostly esters with very low triglycerides and low free fatty acids. This product could be used as biodiesel without further purification.

Example 5

Preparation of Fatty Acid Alkyl Esters from Grease Trap Oil Having High Free Fatty Acid Content Utilising a Catalyst of Formula (I) and Low Cost Mixed Aqueous Alcohols To a 1 litre three-necked round-bottom flask was added 500 grams of bleached and rinsed grease trap oil. The oil had a free fatty acid content of about 78% and an acid value of 156. 50.0 grams of 20% sulfuric acid in methanol, 80.0 grams of 92% fusel oil, 50.0 grams of 80% ethanol, 5.0 grams of catalyst and 5.2 grams of water were then added. The flask was equipped with a water-cooled condenser, thermometer, stoppered injection/sampling point and a magnetic stirrer. The mixture in the flask was heated to a temperature of 83° C. for a period of 3 hours. After this time period the acid value was 16.8. Heating was ceased and the reaction was allowed to stand leading to phase separation. The upper layer comprising the esters was separated and washed with 50.0 grams of water. The acid value was 15.0. Thin layer chromatography analysis of the product shows mostly esters (>90%) with substantially reduced triglycerides and low free fatty acids.

Example 6

Preparation of Fatty Acid Alkyl Esters from Grease Trap Oil having High Free Fatty Acid Content in the Absence of a Catalyst of formula (I) and Low Cost Mixed Aqueous Alcohols To a 1 litre three-necked round-bottom flask was added 500 grams of bleached and rinsed grease trap oil. The oil had a free fatty acid content of about 78% and an acid value of 156. 50.0 grams of 20% sulfuric acid in methanol, 80.0 grams of 92% fusel oil, 50.0 grams of 80% ethanol and 5.2 grams of water were then added. The flask was equipped with a water-cooled condenser, thermometer, stoppered injection/sampling point and a magnetic stirrer. The mixture in the flask was heated to a temperature of 80° C. for a period of 7 hours. Heating was ceased and the reaction was allowed to stand leading to phase separation. The bottom aqueous layer was removed leaving the upper layer containing the esters. The acid value was 19.2. Thin layer chromatography analysis of the product shows mostly esters with some triglycerides and high free fatty acids.

It is apparent that when the catalyst is omitted the reaction rate is much slower and the conversion of free fatty acids is substantially reduced. The catalyst enables a faster conversion rate and increases ester content by virtue of in situ transesterification.

Example 7

Preparation of Fatty Acid Alkyl Esters from Palm Sludge Oil Having Medium Free Fatty Acid Content Utilising a Catalyst of Formula (I) and Low Cost Mixed Aqueous Alcohols To a 1 litre three-necked round-bottom flask was added 500 grams of palm sludge oil. The oil had a free fatty acid content of about 37% and an acid value of 74.7. 50 grams of 20% sulfuric acid in methanol, 80.0 grams of 92% fusel oil, 50.0 grams of 80% ethanol, 5.0 grams of catalyst and 8.8 grams of water were then added. The flask was equipped with a water-cooled condenser, thermometer, stoppered injection/sampling point and a magnetic stirrer. The mixture in the flask was heated to a temperature of 80° C. for a period of 3 hours. After this time period the acid value was 12.8. Heating was ceased and the reaction was allowed to stand leading to phase separation. The upper layer comprising the esters was separated. To this upper layer was added 50.0 grams of 20% sulfuric acid in methanol, 60 grams of dry methanol, 5.0 grams of catalyst and 5.0 grams of water. The mixture was heated to a temperature of 77° C. for a period of 2 hours. The upper layer comprising the esters was bleached with 10.0 grams of sodium chlorite. The recovered product has an acid value of 6.2. Thin layer chromatography analysis of the product shows moderate esters with some triglycerides and low free fatty acids.

Example 8

Preparation of Fatty Acid Ethyl Esters From Tallow Utilising a Catalyst of Formula (I)

To a 1 litre three-necked round-bottom flask was added 500 grams of tallow. The tallow had a free fatty acid content of about 2.5% and an acid value of 5.09. 50.0 grams of 20% sulfuric acid in aqueous ethanol, 110 grams of 80% ethanol, and 10.0 grams of catalyst were then added. The flask was equipped with a water-cooled condenser, thermometer, stoppered injection/sampling point and a magnetic stirrer. The mixture in the flask was heated to a temperature of 80° C. for a period of 3 hours. After this time period the acid value was 5.0. Thin layer chromatography analysis of the product shows medium esters with medium triglycerides and low free fatty acids.

Example 9

Preparation of Fatty Acid Ethyl Esters From Tallow in the Absence of a Catalyst of Formula (I)

To a 1 litre three-necked round-bottom flask was added 500 grams of tallow. The tallow had a free fatty acid content of about 2.5% and an acid value of 5.09. 50.0 grams of 20% sulfuric acid in aqueous ethanol and 110 grams of 80% ethanol were then added. The flask was equipped with a water-cooled condenser, thermometer, stoppered injection/sampling point and a magnetic stirrer. The mixture in the flask was heated to a temperature of 80° C. for a period of 3 hours. After this time period the acid value was 4.5. Thin layer chromatography analysis of the product shows very low esters, very high triglycerides and low free fatty acids.

From Examples 8 and 9 it is apparent that the catalyst promotes transesterification.

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavor to which this specification relates.

It will be appreciated by those skilled in the art that numerous variations and/or modifications may be made to the invention without departing from the spirit or scope of the invention as broadly described. The present embodiments are therefore to be considered in all respects as illustrative and not restrictive.

The invention claimed is:

1. A process for preparing fatty acid alkyl esters comprising:

i) forming a mixture comprising a triglyceride-containing feedstock, water, an alcohol, an acid and a sulfonated fatty acid derivative of the formula (I) or a salt thereof:

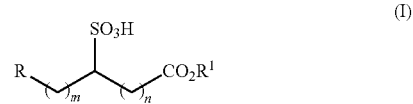

wherein:
n is an integer between 0 and 7,
m is an integer between 6 and 17,
R is hydrogen or methyl,
R1 is hydrogen or C1-C6 alkyl;

ii) allowing the mixture in step i) to react so as to produce a mixture comprising fatty acid alkyl esters; and iii) isolating the fatty acid alkyl esters obtained in step ii, wherein esterification and transesterification occur simultaneously, and wherein the acid is selected from the group consisting of: hydroiodic acid, hydrochloric acid, hydrobromic acid, nitric acid, sulfuric acid and phosphoric acid.

2. The process of claim 1, wherein the triglyceride-containing feedstock comprises at least 20% by weight of free fatty acids.

3. The process of claim 1, wherein the alcohol is present in the mixture in an amount between 10% and 60% by weight.

4. The process of claim 3, wherein the alcohol is present in the mixture in an amount between 15% and 40% by weight.

5. The process of claim 1, wherein the sulfonated fatty acid derivative is present in the mixture in an amount between 0.05% and 5% by weight.

6. The process of claim 5, wherein the sulfonated fatty acid derivative is present in the mixture in an amount between 0.5% and 2.5% by weight.

7. The process of claim 1, wherein the acid is present in the mixture in an amount between 0.5% and 5% by weight.

8. The process of claim 1, wherein the acid is sulfuric acid.

9. The process of claim 1, wherein the water is present in the mixture in an amount of up to about 10% by weight.

10. The process of claim 1, wherein the alcohol is a C1-C12 alcohol, or a mixture thereof.

11. The process of claim 10, wherein the alcohol is methanol, ethanol, propanol, isopropanol, fusel alcohol, or a mixture thereof.

12. The process of claim 1, wherein step ii) comprises heating the mixture.

13. The process of claim 1, wherein in the sulfonated fatty acid derivative n is an integer between 0 and 3.

14. The process of claim 13, wherein n is 0.

15. The process of claim 1, wherein in the sulfonated fatty acid derivative R1 is methyl.

16. The process of claim 1, wherein in the sulfonated fatty acid derivative R is methyl.

17. The process of claim 1, wherein in the sulfonated fatty acid derivative m is an integer between 8 and 17, n is 0, 1 or 2 and R and R1 are methyl.

18. The process of claim 1, wherein m is an integer between 8 and 15, n is 0 and R and R1 are methyl.

19. The process of claim 1, wherein m is an integer between 11 and 15, n is 0 and R and R1 are methyl.

20. The process of claim 1, wherein the mixture comprises a plurality of sulfonated fatty acid derivatives.

21. The process of claim 20, wherein the plurality of sulfonated fatty acid derivatives are $C_{14}$-$C_{18}$ α-sulfonated fatty acid methyl esters, or salts thereof.

22. The process of claim 20, wherein the plurality of sulfonated fatty acid derivatives are $C_{16}$-$C_{18}$ α-sulfonated fatty acid methyl esters, or salts thereof.

23. The process of claim 1, further comprising bleaching and/or degumming the triglyceride-containing feedstock prior to use in step i).

24. The process of claim 1, wherein fatty acid alkyl esters isolated in step iii) have a purity of at least 70%.

25. The process of claim 1, wherein fatty acid alkyl esters isolated in step iii) are not subjected to further purification.

26. The process of claim 1, wherein the triglyceride-containing feedstock comprises at least 60% by weight of free fatty acids.

27. The process of claim 1, wherein the water is present in the mixture in an amount of up to about 5% by weight.

\* \* \* \* \*